United States Patent [19]

Simpson et al.

[11] Patent Number: 5,254,386
[45] Date of Patent: Oct. 19, 1993

[54] DEODORIZED CARPETS AND PROCESS FOR PRODUCING SAME

[75] Inventors: Madeline P. Simpson, Flemington; Raymond S. Brown, Bridgewater, both of N.J.

[73] Assignee: Church & Dwight Co., Inc., Princeton, N.J.

[21] Appl. No.: 698,722

[22] Filed: May 10, 1991

[51] Int. Cl.$^5$ .................. B32B 3/02; D04H 11/00; D05C 17/00; B05D 1/36

[52] U.S. Cl. ........................ 428/95; 428/85; 428/96; 428/97; 427/332; 427/412

[58] Field of Search ............ 428/85, 95, 96, 97; 427/412, 332

[56] References Cited

U.S. PATENT DOCUMENTS

| | | | |
|---|---|---|---|
| 321,368 | 6/1885 | Jossa | 424/76.9 |
| 1,172,297 | 2/1916 | McComb et al. | 252/115 |
| 2,073,831 | 9/1935 | Cohen et al. | 428/95 |
| 3,317,372 | 5/1967 | Hart | 424/76.21 |
| 3,669,819 | 6/1972 | Bischoff | 428/85 |
| 4,008,688 | 2/1977 | Nicholas | 428/95 X |
| 4,110,504 | 8/1978 | Hull et al. | 428/97 |
| 4,298,637 | 11/1981 | Daniel et al. | 428/96 X |
| 4,304,675 | 12/1981 | Corey et al. | 252/8.6 |
| 4,355,065 | 10/1982 | DeMott | 428/96 X |
| 4,371,577 | 2/1983 | Sato et al. | 428/96 |
| 4,608,289 | 8/1986 | McIntosh | 428/95 |
| 4,797,318 | 1/1989 | Brooker et al. | 428/283 |
| 4,931,360 | 6/1990 | Hoshino et al. | 428/328 |
| 4,992,326 | 2/1991 | Dabi | 428/283 |

Primary Examiner—George F. Lesmes
Assistant Examiner—Terrel Morris
Attorney, Agent, or Firm—Bryan Cave

[57] ABSTRACT

The present invention relates to a self-deodorizing carpet and to a deodorizing composition used in the production of a tufted carpet floor covering material. More particularly, the present invention relates to the use of a particular bicarbonate-containing solution containing a water soluble latex for the treatment of tufted carpet floor covering products to impart self-deodorizing properties thereto.

8 Claims, No Drawings

DEODORIZED CARPETS AND PROCESS FOR PRODUCING SAME

TECHNICAL FIELD

The present invention relates to a self-deodorizing carpet and to a deodorizing composition used in the production of a tufted carpet floor covering material. More particularly, the present invention relates to the use of a particular bicarbonate-containing solution for the treatment of tufted carpet floor covering products to impart self-deodorizing properties thereto.

BACKGROUND OF THE INVENTION

The present invention relates to tufted carpet floor covering materials which are conventionally constructed by stitching carpet yarn into a loosely woven sheet of material usually referred to as the primary carpet backing material. This material is normally woven from natural materials such as jute or synthetic materials such as polypropylene and polyethylene. Following stitching of the carpet yarn into the primary backing material, the product has an upper surface with a face of carpet yarn and an undersurface with rows of tuft loop backs of carpet yarn. In order to secure the carpet yarn in place in the primary backing, a layer of a suitable adhesive composition is then spread over the loop backs. This adhesive serves to secure the yarn in place within the primary backing material. In some forms of carpet construction a second woven layer of backing material is then placed on top of the primary layer of adhesive, which is on the back or undersurface of the carpet in order to finish the carpet product. This second woven layer is conventionally referred to as the secondary backing.

In other forms of carpet construction the adhesive composition is spread on the back or undersurface of the carpet product in sufficient quantities to adhere the loops of carpet yarn in place and provide an integral secondary backing. Often in these forms of construction the layer of adhesive composition coating the back is foamed to provide an additional cushion effect. In still other forms of construction, a layer of foam material is placed on top of a layer of adhesive which has been coated on the primary backing to finish the carpet product. The common feature of all forms of tufted carpet is the use of a suitable adhesive composition to secure the tuft loops in place and optionally secure additional layers of other materials to the carpet product.

Tufted carpet has been popular because of the inherent sound deadening features and also the attractive appearance and ease of maintenance for such floor coverings. However, tufted carpet, both residential and commercial, has long been recognized as a sink for odors. In addition to odors from normal dust and dirt, tufted carpet is highly susceptible to acquiring odors from feet, pets, cooking food, spills, smoke and mold and mildew. Carpet cleaners, e.g., vacuums, steam cleaners, spray foams, etc. have long been used to deodorize as well as clean. Relatively recently, carpet deodorizers were introduced to combat odors already in the carpets. These products were predominantly based on fragrances to mask the malodor. The products also contained various levels of sodium bicarbonate to actually deodorize the malodors in the carpet through neutralization and adsorption. None of these devices or products, however, were meant to be odor preventatives.

The deodorization properties of sodium bicarbonate are well-documented. Accordingly, sodium bicarbonate has been topically employed as a deodorant in refrigerators, carpets, personal deodorants and body powders, mouth rinses, aerosol air fresheners, cat litter additives, drain fresheners, etc. Additionally, sodium bicarbonate has a history of being a safe compound, e.g. it is classified as Generally Recognized As Safe—(GRAS), both when taken internally and applied externally to the skin.

Initial attempts at applying sodium bicarbonate as a powder as a permanent deodorizer in tufted carpet was unsatisfactory as the treated carpet would not withstand shipping and handling. Disadvantageously, the bicarbonate powder would accumulate in areas of the carpet and be highly visible and dusty upon installation. Additionally, the powder would be susceptible to removal by normal vacuuming and cleaning. Applying the sodium bicarbonate as a solution to the carpet surface overcame the accumulation and removal drawbacks, but was also highly visible as a powdery residue and also made the carpet feel stiff. Additionally, there were indications that the sodium bicarbonate was reacting with the acid dyes in the carpet and causing slight color changes.

Accordingly, it is an object of the present invention to provide a process which imparts to carpeting, during its manufacture, long term protection against odors developing from common household sources, such as, foot odor, pet odor, smoke odor and the like. This treatment should be resistant to normal vacuuming and steam cleaning and not detract from the aesthetics of the carpeting by unsightly visible accumulations.

This and other objects, features and advantages of the present invention will become apparent from reviewing the following description.

SUMMARY OF THE INVENTION

According to the invention, a bicarbonate salt, preferably, sodium bicarbonate is deposited into the backing or underside of the carpet at the primary backing material prior to the application of the adhesive composition. It is sprayed as a solution, preferably as a saturated solution, onto the primary backing material and allowed to wick or migrate up the carpet fibers. Wicking through the backing material and up the carpet fibers may be controlled by adjusting the viscosity of the solution, contact time, by adding wetting agents or surfactants to the bicarbonate solution, by controlling the relative wetness of the carpet fibers, e.g., after dyeing but prior to spraying the bicarbonate solution, and by adjusting the time the solution is allowed to wick prior to drying, e.g., in an oven. The optimal wicking is about half way up and along the length of the fibers to maximize deodorancy while minimizing visibility and possible interaction with the carpet dye.

An important aspect of the invention is the incorporation of a water-soluble latex into the bicarbonate solution which, advantageously, binds the bicarbonate to the carpet products to deter flaking. Amounts of the water-soluble latex range from about 0.2 to 2.0 and, preferably, from about 0.5 to 1.5 by weight of the total solution.

When applied in this fashion, tests have shown the bicarbonate to be effective in preventing carpets from picking up household odors and yet be resistant to removal by both vacuuming and/or steam cleaning.

DETAILED DESCRIPTION OF THE INVENTION

In accordance with the present invention a tufted carpet product is provided having at least long term, if not permanent, self-deodorizing properties. The intermediate carpet product treated consists of a woven primary backing material and rows of carpet yarn stitched into said primary backing material. The stitching operation produces a product wherein the majority of the carpet yarn is exposed to provide the tufted upper surface of the carpet product. The product also has an undersurface with rows of tuft loop backs protruding through the primary backing to only a slight degree. The tuft loop backs and the undersurface of the carpet product, generally are coated with a liquid carpet adhesive composition which retains the loop backs in place. If sufficient carpet adhesive composition is employed to produce a rather thick and uniform back coating, the carpet product is finished by this back coating operation. Normally, however, a second layer of backing material is adhered to the carpet product by placing a layer of material such as a secondary woven backing on the carpet adhesive composition before the composition has set.

The tufted carpet floor covering materials to which the present invention pertains, generally include at least a primary backing material and carpet yarn stitched into the primary backing material. The bicarbonate solution, as more fully described hereinlater, is applied before a layer of carpet adhesive composition which adheres to the yarn to the primary backing material is applied.

Conventional tufted carpet is prepared from both natural and synthetic and woven and non-woven primary backing materials. In addition the carpet yarn of conventional tufted carpet is manufactured from many natural and synthetic materials such as wool, cotton, nylon, polyester, polyolefin materials and blends thereof and the like.

The carpet adhesive composition used in adhering the yarn include those conventional compositions normally employed in carpet construction such as natural and synthetic latex emulsions, hot melts of polyvinylchloride, polyethylene, polypropylene, and polyesters, aqueous solutions of polymers such as polyvinyl acetate, and like compositions. Synthetic latex emulsions are most commonly employed as the carpet adhesive composition.

The present invention is specifically concerned with the above combination of primary backing material, and stitched carpet yarn with a self-deodorizing bicarbonate solution, preferably saturated, which is applied to the carpet backing, e.g., by spraying. The solution is preferably applied to the backing before the adhesive composition or secondary layer of backing material is adhered to the carpet product. It has been found that the self-deodorizing solution wicks or migrates through the carpet backing and up through and along the carpet yarn or fiber. Preferably, the wicking is about half up the carpet yarn or fibers so as to maximize the deodorizing properties while minimizing visibility and possible interaction with the carpet dyes. The wicking is controlled by: adjusting the solution viscosity, the addition of wetting agents or surfactants to the solution, the relative wetness of the carpet fibers, e.g., after dyeing but prior to spraying the bicarbonate solution, and by adjusting the time the solution is allowed to migrate or wick prior to drying, e.g., in an oven.

According to the present invention, the carpet backing is treated with an aqueous saturated solution containing one or more bicarbonate salts, e.g., alkali metal bicarbonates. While an aqueous solution which is less than saturated is contemplated, concentrations which provide solutions which are less than saturated are not preferred and may incur deodorizing deficiencies.

Suitable bicarbonate salts include sodium bicarbonate, potassium bicarbonate and ammonium bicarbonate, and mixtures of one or more bicarbonates may be employed. A saturated solution of sodium bicarbonate contains about 8% by weight of bicarbonate, a saturated solution of potassium bicarbonate contains about 26% by weight of bicarbonate, and a saturated solution of ammonium bicarbonate contains about 12% by weight of bicarbonate. Alkali metal carbonates and/or sesqui carbonates are not contemplated by the present invention inasmuch as such compounds do not exhibit the advantageous deodorizing characteristics of the bicarbonates. They also may exhibit undesirable physical properties, e.g. a pH sufficiently high to possibly damage carpet yarns and dyes, etc.

In accordance with the present invention, a suitable amount of a water based polymer in latex form is mixed with the bicarbonate salt solution. The latex is added to ensure bonding the bicarbonate and preclude its flaking and concomitant loss of deodorizing capability.

Suitable polymers include natural rubber, synthetic C4-C6 conjugated diolefin containing polymers, acrylic polymers, mixtures thereof and mixtures of vinyl acetate polymers with C4-C6 conjugated diolefin-containing polymers. Preferred among the polymers are C4 conjugated diolefin-containing polymers including polychloroprene, butadiene-styrene polymers and polymers of butadiene, styrene, and one or more ethylenically unsaturated carboxylic monomers. Suitable ethylenically unsaturated carboxylic monomers include acrylic, methacrylic, cinnamic, crotonic, itaconic, maleic, fumaric and atropic acids, the C1-C6 alkyl esters of the aforesaid acids, acrylamide, methacrylamide, N-methylolacrylamide and mixtures of such monomers.

Polymers of butadiene styrene and one or more ethylenically unsaturated carboxylic monomers, which are also known as carboxylated styrene-butadiene rubber (SBR) polymers, are preferred herein.

Carboxylated SBR emulsions useful in the bicarbonate solutions of the present invention are commercially available from a number of suppliers. In addition, the preparation of useful carboxylated SBR emulsions is described in U.S. Pat. No. 3,966,661 to Feast et al., which is incorporated herein by reference.

Briefly, carboxylated SBR emulsions are prepared by emulsion polymerization of butadiene, styrene, and one or more unsaturated acids, such as acrylic acid, methacrylic acid, crotonic acid, maleic acid, fumaric acid, itaconic acid, and 3-butene-1,2,3-tricarboxylic acid. Substituted monocarboxylic acids and substituted polycarboxylic acids may be used if desired. The amount of carboxylic acid used is about 0.5 to 5 percent by weight based on the total monomers. Preferably the carboxylated SBR polymer contains above about one weight percent of such a carboxylic acid monomer. For example, between about one and five weight percent of a carboxylic acid monomer, notably acrylic acid or methacrylic acid. The unsaturated acid may be ethylenically unsaturated monocarboxylic acid, polycarboxylic acid or a mixture of such acids. Preferably, the acids have from two to about ten carbon atoms.

The carboxylated SBR polymer, of which the emulsion is formed, preferably has less than about 50 weight percent bound styrene. For example, between about 20 and 50 weight percent bound styrene, and preferably between about 35 and 50 percent bound styrene.

The treating solutions of the present invention contain from about 0.2 to 2.0 percent by weight, and preferably, about 0.5% to 1.5 and, most preferably, about 0.8 percent by weight of the water soluble polymer latices calculated on an active basis of the polymer content.

The self-deodorizing bicarbonate treatment of the present invention is accomplished by wetting and impregnating the carpet backing with solution and allowing said solution to migrate or wick through the fibers comprising the carpet tufting. Optimally, the wicking is about half way up and along the length of the fiber tufting so as to maximize the deodorizing properties while minimizing visibility of the bicarbonate and to deter possible interaction with the carpet dye. While the amount of wicking can be diminished, the efficacy of the deodorant is likewise diminished in proportion to the amount of the wicking.

The bicarbonate/latex solutions may be applied to the surface of the carpet backing by any suitable means including spraying or brushing. The bicarbonate/latex content in the solution or the amount of solution applied may be adjusted so as to achieve a desired target. Broadly, the target amount of bicarbonate applied is from about 0.5 to 2.0 percent by weight of the carpet weight to which it is applied. Preferably, the target range of applied bicarbonate is about 0.75 to 1.5 and, most preferably, about 1.0 percent by weight based on the carpet weight. By carpet weight is meant the combined weight of the carpet backing material and the fibers tufted thereon. The target amount of water-soluble polymer latex is generally from about 0.05 to 0.25, preferably, from about 0.075 to 0.15 and, most preferably, about 0.1 percent by weight based on the carpet weight.

One means of controlling the wicking is by adjusting and raising the viscosity of the bicarbonate solution. One such method is by incorporating an organic and/or inorganic thickening agent into the bicarbonate solution. Generally, the organic thickeners comprise a class of high-molecular weight molecules, usually with collidal properties, which in an appropriate solvent are able to produce a gel at low dry-substance content. Various rubbers, as are many synthetic polymers, are suitable for use as thickeners herein. The preferred organic thickeners, however, are the xanthan and/or guar gums. Such gums are especially desirable as they possess the property of being permanently pliable and not subject to rigidizing into a brittle substance after a period of time. Inorganic thickening agents include the silica gels. When blending the thickening agent into the bicarbonate solutions, a suitable concentration is from about 0.1 to 2 percent by weight of the bicarbonate solution, preferably, from about 0.2 to 1 percent by weight of the bicarbonate solution.

If desired, a surfactant or wetting agent, preferably a nonionic surfactant, may be incorporated into the bicarbonate solution. A large number of commercial nonionic surfactant are available. Such surfactants comprise high molecular weight alkyl, aryl, or alkyl-aryl groups attached to an ethylene oxide chain. The amounts of nonionic surfactants employed range from about 0.1 up to 2 percent by weight and, preferably, from about 0.2 to 1 percent by weight.

The amount of wicking also depends on the relative wetness of the carpet fibers prior to the treatment with the bicarbonate solution, the length of time the solution is allowed to contact, i.e., wet, the carpet backing and the drying time and temperature utilized, e.g., in an oven, to dry the treated carpet before further processing. All of these operations and/or conditions are within the abilities of one skilled in the art and one having such skill can readily control such conditions so that the desired degree of migration or wicking is obtained.

The following example will further illustrate a specific embodiment of the invention. In this example, all the amounts are given in percent by weight, unless otherwise specified.

EXAMPLE I

The following formulation was prepared according to the present invention.

| Component | Formulation Percent by Weight |
|---|---|
| Sodium Bicarbonate | 8.0 |
| Carboxylated Styrene Butadiene | 0.81 |
| Water | 91.19 |

A tufted carpet product was treated according to the following procedure.

An intermediate carpet product was prepared using nylon carpet yarn and polypropylene for the primary woven backing material. The weight of this intermediate carpet product was 30 ounces per square yard. Following construction and subsequent dyeing of the carpet yarn/backing product, the above solution was applied by spraying onto the undersurface of the carpet backing. The target amount applied was a 13% wet pick-up based on the carpet weight. The resultant amounts applied to the carpet product was 1.040 percent by weight bicarbonate and 0.105 percent by weight polymer latex based on the carpet weight. The carpet product was tested over a period of 6 months and found to be self-deodorizing.

While this invention has been described in detail with particular reference to preferred embodiments thereof, it will be understood that variations and modifications can be affected within the sphere and scope of the invention as described herein before and as defined in the appended claims.

What is claimed is:

1. A self-deodorizing tufted carpet product comprising a primary backing material and rows of a carpet yarn stitched into said primary backing material to produce a face of yarn on one side of the backing and tuft loop backs of yarn on the opposite underside of the backing, wherein sodium bicarbonate in an amount of from about 0.5 to 2.0 percent by weight and a water soluble latex in an amount of from about 0.05 to 0.25 percent by weight, based on the weight of the tufted carpet product, have been deposited within said backing and along about one-half the lower length of said carpet yarn and wherein a layer of carpet adhesive composition has been applied on the treated tuft loop backs and on the treated underside of the backing.

2. The carpet product of claim 1 wherein the water soluble latex is a carboxylated styrene-butadiene latex.

3. The carpet product of claim 1 wherein a surfactant has been deposited with said bicarbonate salt.

4. The carpet product of claim 1 wherein a thickening agent has been deposited with said bicarbonate salt.

5. A process for producing a self-deodorizing tufted carpet product which comprises stitching rows of carpet yarn into a primary backing material to produce a face of yarn on one side of the backing and tuft loop backs of yarn on the opposite underside of the backing, applying a saturated solution of sodium bicarbonate which contains a water soluble latex in an amount of from about 0.2 to 2.0 percent by weight calculated on an active basis of the polymer content to said underside of said backing and allowing the solution to migrate by wicking through said backing and along about one half the lower length of said carpet yarn wherein the sodium bicarbonate is deposited in an amount of from about 0.5 to 2.0 percent by weight and water soluble latex is deposited in an amount of from about 0.05 to 0.25 percent by weight based on the weight of the tufted carpet product to which it is being applied.

6. The process of claim 5 wherein the water soluble latex is a carboxylated styrene-butadiene latex.

7. The process of claim 5 wherein the bicarbonate solution contains a surfactant in an amount of from about 0.1 to 2.0 percent by weight of said solution.

8. The process of claim 5 wherein the bicarbonate solution contains a thickening agent in an amount of from about 0.1 to 2.0 percent by weight based on the weight of solution.

* * * * *